United States Patent
Nakamura et al.

(10) Patent No.: US 6,867,193 B1
(45) Date of Patent: Mar. 15, 2005

(54) AMINO ACID-CONTAINING ALBUMIN PREPARATION

(75) Inventors: Yukio Nakamura, Osaka (JP); Yasuhiro Tsutsui, Osaka (JP); Makoto Sato, Osaka (JP)

(73) Assignee: Nipro Corporation, Osaka (JP)

( * ) Notice: Subject to any disclaimer, the term of this patent is extended or adjusted under 35 U.S.C. 154(b) by 0 days.

(21) Appl. No.: 09/889,604
(22) PCT Filed: Jan. 14, 2000
(86) PCT No.: PCT/JP00/00162

§ 371 (c)(1),
(2), (4) Date: Sep. 19, 2001

(87) PCT Pub. No.: WO00/43035

PCT Pub. Date: Jul. 27, 2000

(30) Foreign Application Priority Data

Jan. 19, 1999 (JP) .......................................... 11/010628

(51) Int. Cl.[7] ........................ A61K 38/00; A61K 35/16; C07K 14/00
(52) U.S. Cl. ............................. 514/21; 514/2; 424/520; 424/531; 530/362; 530/363; 530/364; 530/830
(58) Field of Search ....................... 514/21, 2; 424/520, 424/531; 530/362, 363, 364, 830

(56) References Cited

U.S. PATENT DOCUMENTS 4,499,076 A * 2/1985 Ohashi et al. ............... 424/143

FOREIGN PATENT DOCUMENTS

| DE | 36 22 642 A1 | | 1/1988 |
|---|---|---|---|
| DE | 39 35 906 A1 | | 5/1991 |
| EP | 0 683 233 A2 | | 11/1995 |
| EP | A 0 683 233 | * | 11/1995 |
| FR | 2 574 254 A1 | | 6/1986 |
| WO | 86/03380 A1 | | 6/1986 |
| WO | 88/01861 A1 | | 3/1988 |
| WO | WO 88/01861 | * | 3/1998 |

OTHER PUBLICATIONS

Patent Abstract of Japan, Publication No. 58–126767, Publication Date Jul. 28, 1983.
Patent Abstract of Japan, Publication No. 59–016817, Publication Date Jan. 28, 1984.
Patent Abstract of Japan, Publication No. 62–224259, Publication Date Oct. 2, 1987.
Patent Abstract of Japan, Publication No. 64–083017, Publication Date Mar. 28, 1989.
Patent Abstract of Japan, Publication No. 03–127737, Publication Date May 30, 1991.
Patent Abstract of Japan, Publication No. 05–015339, Publication Date Jan. 26, 1993.
Patent Abstract of Japan, Publication No. 10–158172, Publication Date Jun. 16, 1998.
Patent Abstract of Japan, Publication No. 10–257867, Publication Date Sep. 29, 1998.
JJPEN, 11(9), 1137, 1989.
Shin–yaku to Rinsho, 31, 175–185, 1982.

* cited by examiner

*Primary Examiner*—Jon Weber
*Assistant Examiner*—Abdel A. Mohamed
(74) *Attorney, Agent, or Firm*—Kubovcik & Kubovcik

(57) ABSTRACT

An albumin preparation that prevents onset of hepatic encephalopathy caused by conventional amino acid preparations and enhances an effect of improving the symptoms is provided. The albumin preparation containing amino acids is characterized in that a content of albumin is 0.01 to 1.0 w/v %, a content of plurality of amino acids containing branched amino acid is 5 to 10 w/v %, a content of the branched amino acids is equal to or more than 30 w/w % on the basis of the content of total amino acids and further, the Fischer ratio (branched amino acid/[phenylalanine+tyrosine] (molar ratio)) is equal to or more than 20.

9 Claims, No Drawings

AMINO ACID-CONTAINING ALBUMIN PREPARATION

TECHNICAL FIELD

This invention relates to an albumin preparation useful for treatment of hepatic malfunctions including hepatic encephalopathy, hepatic coma and the like and, especially, to an albumin preparation containing amino acids including a large amount of branched amino acids.

BACKGROUND TECHNIQUES

Hepatic encephalopathy is a complication that is often observed when a hepatic malfunction such as liver cirrhosis, fulminant hepatic failure and the like occurs, and presents various psychoneurosis symptoms. As an early indication of the encephalopathy, such symptoms appear that self-control is not exercised, hypnic rhythm is disturbed, or day and night are mixed up. Subsequently, judgement is lowered and the patient becomes confused, and finally, the patient lapses into a coma and cannot react to an external stimulus.

As to one cause of hepatic encephalopathy, it is taken very seriously that ammonia generated mainly by means of bacteria in an intestine is absorbed into the liver, is not detoxicated therein and is transferred to the brain. Therefore, administration of antibiotics in order to remove the bacteria in the intestine, or administration of lactulose for absorption restraint of ammonia and the like (Japanese Patent Laid-open No. Hei. 10-158172 etc.) is conventionally carried out. However, the efficacy of these treatments is not yet sufficient.

Furthermore, as to other causes, an imbalance of the free amino acids in the blood plasma is noted such that a concentration of aromatic amino acids comprising L-phenylalanine, L-tryptophan, L-tyrosine and the like in the plasma is increased while a concentration of branched amino acids comprising L-leucine, L-isoleucine, L-valine and the like is decreased with severe hepatopathy. This imbalance of the free amino acids in the blood plasma causes an abnormality of amino acid metabolism in the brain such as an abnormality in transporting amino acids into the brain across the blood brain barrier, an inhibition of normal production of neurotransmitters in the brain, and production of pseudo-neurotransmitters. Therefore, there is a view that hepatic encephalopathy is caused.

Therefore, administration of an amino acid preparation containing a large amount of branched amino acids and a reduced amount of aromatic amino acids is carried out as a new treatment (Japanese Examined Patent Publication No. Hei. 3-28403, Japanese Laid-open Patent No. 1-83017, and Japanese Patent Laid-open No. Hei. 3-127737). A preparation comprising such a composition is commercialized as a therapeutic agent for hepatic encephalopathy (JJPEN, 11(9), 1137, 1989). However, this amino acid preparation shows a therapeutic effect of only about 46% on hepatic encephalopathy caused by an acute hepatic insufficiency, and the efficacy is not sufficient (Shin-yaku to Rinsho, 31, 175–185, 1982).

Alternatively, the inventors of the present invention had an idea that if albumin is supplied and a concentration of albumin in the blood is restored on affecting such hepatopathy, amino acids administered as an amino acid preparation will not be consumed for albumin synthesis and the state of an amino acid imbalance will smoothly improve, and as a result, abnormality of amino acid metabolism occurring in the brain with hepatic encephalopathy can be improved rapidly.

An object of the present invention is to provide an amino acid preparation for preventing an onset of hepatic encephalopathy caused by a conventional amino acid preparation and enhancing an effect of amelioration of the symptoms.

DISCLOSURE OF THE PRESENT INVENTION

As a result of intensive research by the present inventors with a view of accomplishing the above-described object, it has been found that addition of albumin into an amino acid preparation containing branched amino acids results in a superior therapeutic effect on hepatic encephalopathy. That is, it has been found that when a concentration of albumin in the blood is restored to a normal status by supplying albumin, amino acids administered simultaneously reduce the imbalance of amino acids without being consumed for synthesis of a protein such as albumin in the liver, thus completing the present invention.

The present invention relates to an amino acid-containing albumin preparation which comprises albumin, a plurality of amino acids including branched amino acids, and water.

Branched amino acids in the present invention include amino acids having a branched alkyl group in the side chain thereof, that is, L-valine, L-leucine or L-isoleucine, and any of these amino acids can be used. Other amino acids are aliphatic amino acids such as straight-chain amino acids (glycine, L-alanine), hydroxy amino acids (L-serine, L-threonine), acidic amino acids (L-aspartic acid, L-glutamic acid), amido-type amino acids (L-asparagine, L-glutamine), basic amino acids (L-lysine, L-hydroxy lysine, L-arginine), and sulfur-containing amino acids (L-cystein, L-cystine, L-methione). Further, aromatic amino acids (L-phenylalanine, L-tyrosine), heterocyclic amino acids (L-tryptophan, L-histidine), heterocyclic imino acid (L-proline) and the like are also included. One or more amino acids among these amino acids can be used. These amino acids can also be used as salts thereof, for instance, chlorides, acetates and the like.

A content of the plurality of amino acids including branched amino acids is 5 to 10% by weight based on the volume of the preparation (w/v %). A content of branched amino acids is equal to or more than 30% by weight based on the weight of total amino acids (w/w %), and the Fischer ratio (branched aminoacid/[phenylalanine+tyrosine] (molar ratio)) is equal to or more than 20. If the content of amino acids is less than 5 w/v %, a therapeutic effect on hepatic disease is not sufficiently accomplished. Also, if the content of amino acids is more than 10 w/v %, the content of the amino acids increases to become insoluble in water, so that it is difficult to produce the preparation. On the other hand, if the content of branched amino acids is less than 30 w/w %, the original properties of the amino acid preparation comprising a large amount of branched amino acids for treating hepatic insufficiency can be diminished. Further, the therapeutic effect on hepatic insufficiency is reduced to diminish the merits of the amino acid preparation for treating hepatopathy if the Fischer ratio is less than 20.

The plurality of amino acids including branched amino acids preferably comprises the following composition.

TABLE 1

Amino acid composition (ratio by weight based on total amino acids)

| amino acid | content ratio (w/w %) |
| --- | --- |
| L-threonine | 2.0 to 6.0 |
| L-serine | 2.0 to 8.0 |
| L-proline | 2.0 to 11.0 |
| L-cysteine | 0 to 2.0 |
| glycine | 1.0 to 12.0 |
| L-alanine | 4.0 to 12.0 |
| L-valine | 10.0 to 14.0 |
| L-methionine | 0 to 2.0 |
| L-isoleucine | 8.0 to 16.0 |
| L-leucine | 10.0 to 17.0 |
| L-phenylalanine | 0 to 2.0 |
| L-tryptophan | 0 to 2.0 |
| L-lysine | 3.0 to 10.0 |
| L-histidine | 1.0 to 5.0 |
| L-arginine | 7.0 to 21.0 |
| L-aspartic acid | 0 to 3.0 |
| L-glutamic acid | 0 to 6.0 |

As a solution comprising the above-described amino acids, a conventional drug preparation, for instance, AMINOLEBAN (produced by Otsuka Pharmaceutical Factory) and MORIHEPAMIN (produced by Hoechst Marion Roussel), and the like is exemplified. The composition of these preparations is already known.

An albumin used in the present invention includes albumin derived from animals, genetic engineered albumin and the like, but is not limited. However, albumin derived from a human is preferable in view of antigenicity. Human serum albumin, genetic engineered human albumin and the like are exemplified as an albumin derived from a human, but ordinarily, an albumin equivalent to albumin for medical use may be used. Albumin treated thermally in order to inactivate viruses is also preferable. It is preferable to add an appropriate additive in order to improve stability of the albumin against heat while being thermally treated. The stabilizer includes, specifically, N-acetyl tryptophan sodium, sodium caprilate and the like. Moreover, in the present invention, genetic engineered albumin is more preferably used in order to avoid virus invasion. The method for preparing the albumin by genetic recombination technology is not especially limited. Normally, a gene which encodes albumin is inserted into a vector and a host cell such as yeast, *Escherichia coli* or an animal cell is transformed with the vector, and the transformed cell is cultivated to collect the genetically recombinant albumin. The albumin can be isolated and purified from the culture supernatant or the cultivated cell. The purity of the albumin is preferably more than 99% of total proteins.

An amount of the albumin used in the present invention is 0.01 to 3 w/v %, and preferably, 0.1 to 1.0 w/v %, in the preparation. If the amount of the albumin is less than 0.01 w/v %, the therapeutic effect on hepatic disease is not enhanced. Also, if the albumin amount its is more than 3 w/v %, there is a probability of causing circulatory diseases such as cardiac overload and lung edema when a large amount of the preparation is rapidly administered.

The preparation of the present invention is a solution containing the above-described amino acids and albumin or a solid agent that is capable of dissolving on application, and is prepared in the form of a sterilized aqueous solution. Ordinarily, these components are dissolved into an injectable distilled water. Therefore, the preparation has a pH of 5.0 to 7.4, preferably, a pH of 6.0 to 7.4, in view of the pH of human body fluid. An acid such as hydrochloric acid, acetic acid, citric acid, and malic acid is used as a pH adjuster.

Further, a required amount of vitamins, for instance, vitamins such as vitamin A, B1, B2, B6, C, D, E, nicotinic acid, pantothenic acid, biotin, folic acid and vitamin-like compounds, electrolytes such as sodium, potassium, calcium, chloride, phosphorus, and trace elements such as iron, zinc, manganese, copper, iodine, selenium can be added to the albumin preparation in the present invention.

Also, nutrients such as sugars, for instance, maltose, fructose and xylitol, and lipids, for instance, soybean oil, cottonseed oil and sesame oil can be added.

In addition, stabilizers such as sodium bisulfite, or agents which can be administered into a human body can be added.

As the albumin preparation in the present invention, there exists a one-formulation type (e.g., one liquid formulation in which the total components are dissolved), two-formulation type (e.g., two preparations comprising a liquid formulation in which amino acids are dissolved and an albumin preparation) or the like.

A vessel for containing the albumin preparation of the present invention includes, for instance, a plastic bag comprising one or two chambers, or one or two glass vessels or a plastic bag comprising one chamber and, in addition, a combination of a plastic bag and a glass vessel. As an example, all of the components of the albumin preparation of the present invention are dissolved into injectable distilled water and the solution may be filled into one chamber of a plastic bag, or separate components may be filled into both upper and lower ones of two chambers. Specifically, the vessel is a flexible plastic bag that is a so called "double bag" which comprises upper and lower chambers separated with a heat-sealed portion in a band-shape which can be easily peeled by strongly pressing the bag by hand. Each chamber provides an inlet and an outlet for the preparation. The lower chamber of this bag is filled with a solution containing amino acids and the upper chamber is filled with a powder, a solid or a solution comprising albumin. Another vessel includes an injection cylinder or a pre-filled syringe, in which an albumin solution is filled, and the albumin preparation filled in the cylinder or the syringe and an amino acids preparation filled in a bag can be used as a kit preparation.

A method for producing the preparation of the present invention is one in which albumin, for instance, an albumin aqueous solution or lyophilized albumin, is added to a solution containing the above-mentioned amino acids.

The preparation of the present invention containing the respective components is required to be sterilized. Methods for sterilization include regular high-pressure steam sterilization, sterilization heated under lower temperature, filtration sterilization and the like, alone or as a combination thereof.

Additionally, the albumin preparation of the present invention can be administered intravenously into a peripheral vein, a central vein or the like, and is used by appropriately increasing or decreasing the preparation so as to be administered once or twice per day in consideration of condition, nutritional status, age, bodyweight, etc. of the patient to be administered aiming that, generally, a preparation of about 100 to 200 ml, preferably about 500 to 1000 ml, per adult per day can be administered.

THE BEST MODE TO CARRY OUT THE INVENTION

The present invention will be illustrated in detail by the Examples.

PREPARATION EXAMPLE 1

An albumin preparation containing the following components was prepared.

Amino acid solution (components are disclosed in Table 2) 500 ml

Rat serum albumin (RSA, manufactured by Sigma Corp.) 1 g

According to the above formula, the components were dissolved, and then the pH of the solution was adjusted to 6.6 to 7.4 using 1.0 N hydrochloric acid to prepare the albumin preparation. The osmotic pressure ratio was 2.8 to 3.2. This drug solution was introduced into a 500 ml infusion bottle and closed with a rubber plug, and thermally sterilized at 60° C. for 10 hours. The drug solution after sterilization had a pH of 6.6 to 7.4 and an osmotic pressure ratio of 2.8 to 3.3.

TABLE 2

Unit: an amount (mg) of amino acid dissolved in 100 ml injectable distilled water

| | |
|---|---|
| L-threonine | 450 |
| L-serine | 500 |
| L-proline | 800 |
| L-cystein hydrochloride (monohydrate) | 40 |
| glycine | 900 |
| L-alanine | 750 |
| L-valine | 840 |
| L-methione | 100 |
| L-isoleucine | 900 |
| L-leucine | 1100 |
| L-phenylalanine | 100 |
| L-tryptophan | 70 |
| L-lysine chloride | 760 |
| L-histidine chloride | 320 |
| L-arginine chloride | 730 |

PREPARATION EXAMPLE 2

The following albumin preparation was prepared.
A. Amino acid solution (components are disclosed in Table 3) 980 ml
B. 12.5 w/v % commercialized human serum albumin preparation 20 ml The above-mentioned amino acid solution A was dissolved in injectable distilled water so as to adjust the pH of the preparation to 6.6 to 7.4 and was filled in a lower chamber of a double-bag and thermally sterilized at 121° C. for 30 minutes after sealing the bag. On the other hand, the albumin preparation B (12.5 w/v % albumin) was filled in a lower chamber of the double bag and sterilized at 60 Co for 10 hours. When used, the two solutions in the double bag were mixed. The drug solution after they were mixed had a pH of 6.6 to 7.4 and an osmotic pressure ratio of 2.8 to 3.3.

TABLE 3

Unit: an amount (mg) of amino acid dissolved in 100 ml of injectable distilled water

| | |
|---|---|
| L-threonine | 214 |
| L-serine | 260 |
| L-proline | 530 |
| glycine | 540 |
| L-alanine | 840 |
| L-valine | 890 |
| L-methione | 44 |
| L-isoleucine | 920 |
| L-leucine | 945 |
| L-phenylalanine | 30 |
| L-tryptophan | 70 |
| L-arginine chloride | 1537 |
| L-asparatic acid | 20 |
| L-histidine | 310 |
| L-lysine acetate | 395 |
| L-tyrosine | 40 |

PREPARATION EXAMPLE 3

Amino acid solution (components are disclosed in Table 3) 500 ml

Human serum albumin (HSA, manufactured by Sigma Corp.) 0.05, 0.5 or 5.0 g

The above-mentioned formulation was dissolved in injectable distilled water, the pH adjusted to 6.6 to 7.9 using 1.0 N hydrochloric acid, filtered with a membrane filter having a pore diameter of 22 μm to remove bacteria and filled in a plastic bag. This preparation was preserved in a sealed vessel at room temperature while being shaded. The drug solution after being filled had a pH of 6.6 to 7.4 and an osmotic pressure ratio of 2.8 to 3.3.

TEST EXAMPLE 1

A test drug was prepared by dissolving rat serum albumin (RSA, manufactured by Sigma Corp.) in an amino acid solution (components are disclosed in Table 3) to form a 0.1 w/v % or 1.0 w/v % solution, adding 1.0 N hydrochloric acid thereto to adjust the pH to 6.6 to 7.4 according to Preparation Example 3, filling the solution into a 500 ml infusion bottle and heating at 60° C. for 10 hours after sealing the bottle with a rubber plug. In comparison, physiological saline or the amino acid solution (pH 6.6 to 7.4), respectively, was used in the same way.

Rat partial hepatectomy was carried out by performing a laparotomy of a male SD rat (body weight of 200 to 230 g) under etherization, removing a lateral left lobe, a medial left lobe and a medial right lobe (67%) and closing the abdomen (Archs. Pathol., 1985; 12: 186–202).

A hepatic encephalopathy model animal was created by administering 2 M ammonium acetate solution at a rate of 3 ml/kg into the rat abdomen after 48 hours from the partial hepatectomy ("Kiso to Rinsho", 1987; 21: 2509–2527).

The test drug was injected from the rat tail vein (10 ml/kg) 2 minutes before administering the ammonium solution. Subsequently, the coma period (minutes) was measured, blood was collected from the rat tail vein 30 minutes after administration of the ammonium solution, and the ammonia concentration in the blood plasma was determined by using an ammonia measuring reagent kit (brand name: Determiner $NH_3$, manufactured by Kyowa Medics Corporation). The results are shown in Table 4.

As well, the creation of a hepatic encephalopathy model animal was confirmed by a coma of the rat resulting from administrating an ammonium acetate solution thereto.

TABLE 4

| composition | administration of ammonia | number of animals | coma period (min) | concentration of ammonia in the blood ($\mu$mol/dL) |
|---|---|---|---|---|
| Physiological saline | − | 6 | 0 | 11 ± 2 |
| Physiological saline (control group) | + | 7 | 38 ± 6 | 154 ± 14 |
| 1.0% RSA | + | 5 | 31 ± 5 | 129 ± 13 |
| amino acid solution | + | 6 | 25 ± 4 | 105 ± 5* |
| amino acid solution + 0.1% RSA | + | 6 | 14 ± 2#** | 91 ± 3#** |
| amino acid solution + 1.0% RSA | + | 5 | 12 ± 4#** | 91 ± 3#** |

Numbers show mean value ± standard error.
The concentration of RSA shows the final concentration.
*:P < 0.05, **:P < 0.01, There is a significant difference compared with the physiological saline group (control group).
:P < 0.05; There is a significant difference compared with the group in which amino acid solution alone was administered.

As apparent from Table 4, the rat serum albumin (RSA) alone had no effect on the hepatic encephalopathy. The amino acid solution alone showed a significant effect of reducing ammonia concentration in the blood and a tendency to decrease the coma period compared with the control group although there was no significant difference. On the other hand, the albumin preparation in the present invention showed a significant effect on decreasing of the coma period and reducing ammonia concentration in the blood, and thus the enhancement of a therapeutic effect towards hepatic coma was recognized.

TEST EXAMPLE 2

A test drug was prepared by dissolving human serum albumin (HSA, manufactured by Sigma Corp.) in the amino acid solution (components are disclosed in Table 3) in the same manner as in Preparation Example 3 to form a desired concentration of the solution (0.001, 0.01, 0.1 or 1.0 w/v %). 6 to 14 male SD rats (body weight 200 to 230 g) as test animals were used per one group, and creation of a hepatic encephalopathy model animal and a test method were carried out in the same manner as Test Example 1. The test drug was injected in an amount of 10 ml/kg from the tail vein.

TABLE 5

| composition | number of animals | coma period (min) | concentration of ammonia in the blood ($\mu$mol/dL) |
|---|---|---|---|
| Physiological saline | 10 | 37 ± 12 | 117 ± 11 |
| 1.0% HSA | 10 | 33 ± 10 | 116 ± 12# |
| Amino acid solution | 10 | 28 ± 9 | 92 ± 12* |
| Amino acid solution + 0.001% HSA | 10 | 24 ± 8 | 91 ± 11* |
| Amino acid solution + 0.01% HSA | 8 | 17 ± 6#** | 87 ± 13** |
| Amino acid solution + 0.1% HSA | 7 | 11 ± 6##** | 82 ± 11#** |
| Amino acid solution + 1.0% HSA | 7 | 6 ± 4##** | 79 ± 12##** |

Numbers show mean value ± standard error.
The concentration of HSA shows the final concentration.
*:P < 0.05, **:P < 0.01, There is a significant difference compared with the physiological saline group (control group).
:P < 0.05; ##: P < 0.01; There is a significant difference compared with the group in which amino acid solution was administered.

As apparent from Table 5, while the amino acid solution had no significant effect of decreasing the coma period compared with the control group, the ammonia concentration in the blood was reduced significantly. On the other hand, the HSA alone showed no effect on the coma period or the ammonia concentration in the blood. However, the albumin preparation in which more than 0.01 w/v % of HSA was added to the amino acid solution in the present invention showed a significant effect on decreasing of the coma period and reducing the ammonia concentration in the blood.

TEST EXAMPLE 3

A test drug was prepared by dissolving bovine serum albumin (BSA, manufactured by Sigma Corp.) in the amino acid solution (components are disclosed in Table 3) in the same manner as in Preparation Example 3 to form a desired concentration of the solution (0.1 w/v % or 1.0 w/v %). Creation of a hepatic encephalopathy model animal and a test method were carried out in the same manner as Test Example 1. The results are shown in Table 6.

TABLE 6

| composition | number of animals | coma period (min) | concentration of ammonia in the blood ($\mu$mol/dL) |
|---|---|---|---|
| Physiological saline | 8 | 30 ± 3 | 123 ± 7 |
| 1.0% BSA | 6 | 23 ± 3 | 119 ± 10 |
| Amino acid solution | 6 | 17 ± 2** | 94 ± 9* |
| Amino acid solution + 0.1% BSA | 6 | 7 ± 3**# | 100 ± 4* |
| Amino acid solution + 1.0% BSA | 6 | 5 ± 3**## | 69 ± 13** |

Numbers show mean value ± standard error.

As apparent from Table 6, the albumin preparation in the present invention showed a significant effect on decreasing of the coma period compared with the amino acid solution alone.

TEST EXAMPLE 4

A test drug was prepared by dissolving human serum albumin in the amino acid solution (components are disclosed in Table 3) in the same manner as in Preparation Example 3 to form a desired concentration (0.01, 0.1, 1.0 w/v %) of the solution. 5 male SD rats (body weight 200 to 230 g) as test animals were used per one group. Ammonia encephalopathy model animals were created by partially removing the liver and then administering 2 M ammonium acetate solution. The test drug was injected to an abdominal aorta in an amount of 10 ml/kg 2 minutes before administration of the ammonium solution. After 1.5 hours from the administration of the ammonium solution, the blood was collected from the abdominal aorta under etherization. An equivalent volume of 5 w/v % trichloroacetic acid solution was promptly added into the blood to centrifuge and, thereafter, the supernatant was measured using an amino acid analyzer (D-7000, manufactured by Hitachi) to determine the free amino acid concentration in the serum. The Fischer ratio was determined from the amino acid concentration in the serum. The results are shown in Table 7.

TABLE 7

| Component | number of animals | concentration of amino acid in the blood (μmol/dL) | Fischer ratio |
|---|---|---|---|
| Physiological saline | 5 | 8.1 ± 0.6 | 0.80 ± 0.48## |
| 1% HSA | 5 | 8.2 ± 0.8 | 0.97 ± 0.27## |
| Amino acid solution | 5 | 11.0 ± 1.0** | 2.15 ± 0.12** |
| Amino acid solution + 0.01% HSA | 5 | 10.8 ± 0.8** | 2.97 ± 0.31#** |
| Amino acid solution + 0.1% HSA | 5 | 10.8 ± 0.7** | 3.70 ± 0.45##** |
| Amino acid solution + 1.0% HSA | 5 | 11.3 ± 1.2** | 3.20 ± 0.5##** |

Numbers show mean value ± standard error.
The concentration of HSA shows the final concentration.
**: There is a significant difference ($P < 0.01$) compared with physiological saline group.
: There is a significant difference ($P < 0.01$) compared with the group in which the amino acid solution alone was administered.

The Fischer ratio of a normal rat was in the range of 3 to 4. In the physiological saline group, the Fischer ratio was extremely low as well as those in human serious hepatopathy and hepatic cirrhosis. The Fischer ratio was not improved in the group of 1 w/v % HSA but a significant improvement was recognized in the amino acid solution group. Further, the group of the albumin preparation of the present invention (amino acid solution+0.01, 0.1 or 1 w/v % RSA) showed a ski significant improvement compared with the other respective administration groups.

From the above results, it is apparent that the albumin preparation containing amino acids of the present invention has a positive effect towards the reduction of amino acids concentration in the blood and their imbalance which occurs in liver diseases.

INDUSTRIAL UTILIZATION

As mentioned above, compared with the administration of only amino acid solution, the albumin preparation of the present invention can reduce more significantly the ammonia concentration in the blood of a model animal suffering from hepatic encephalopathy, and decrease the coma period. Therefore, the albumin preparation of the present invention is considered to have excellent effect in treatment against failure of the liver functions including hepatic encephalopathy, hepatic coma and the like.

What is claimed is:

1. An albumin preparation comprising human serum albumin, a plurality of amino acids comprising branched amino acids and water, said preparation being in a form suitable for administration to a patient for treatment of liver diseases.

2. An albumin preparation as claimed in claim 1, wherein the content of the human serum albumin is 0.01 to 1.0 w/v %.

3. An albumin preparation as claimed in claim 1, wherein the content of said plurality of amino acids containing branched amino acids is 5 to 10 w/v %.

4. An albumin preparation as claimed in claim 1, wherein the content of the branched amino acids is equal to or more than 30 w/w % on the basis of a content of total amino acids, and a Fischer ratio (branched amino acid/[phenylalanine+tyrosine] (molar ratio)) is equal to or more than 20.

5. An albumin preparation as claimed in claim 1, wherein the content of the human serum albumin is 0.01 to 1.0 w/v %, the content of said plurality of amino acids comprising branched amino acids is 5 to 10 w/v %, the content of the branched amino acids is equal to or more than 30 w/w % on the basis of a content of total amino acids, and a Fischer ratio (branched amino acid/[phenylalanine+tyrosine] (molar ratio)) is equal to or more than 20.

6. The albumin preparation as claimed in claim 1, wherein said preparation is in the form of a sterilized aqueous solution.

7. A method of treating liver diseases comprising administering an albumin preparation as claimed in claim 1 to a patient in need of such treatment.

8. An albumin preparation comprising 0.01 to 1.0 w/v % of human serum albumin, 5 to 10 w/v % of a plurality of amino acids comprising branched amino acids, a content of branched amino acids of 30 w/w % or more on the basis of a content of total amino acids, and a Fischer ratio (branched amino acid/[phenylalanine+tyrosine] (molar ratio)) of 20 or more, the plurality of amino acids having the following composition:

| amino acid | content ratio (w/w %) |
|---|---|
| L-threonine | 2.0 to 6.0 |
| L-serine | 2.0 to 8.0 |
| L-proline | 2.0 to 11.0 |
| L-cysteine | 0 to 2.0 |
| glycine | 1.0 to 12.0 |
| L-alanine | 4.0 to 12.0 |
| L-valine | 10.0 to 14.0 |
| L-methionine | 0 to 2.0 |
| L-isoleucine | 8.0 to 16.0 |
| L-leucine | 10.0 to 17.0 |
| L-phenylalanine | 0 to 2.0 |
| L-tryptophan | 0 to 2.0 |
| L-lysine | 3.0 to 10.0 |
| L-histidine | 1.0 to 5.0 |
| L-arginine | 7.0 to 21.0 |
| L-aspartic acid | 0 to 3.0 |
| L-glutamic acid | 0 to 6.0 |
| L-tyrosine | 0 to 1.0 | the content ratio being a ratio by weight to total amino acids, said preparation being in a form suitable for administration to a patient for treatment of liver diseases.

9. The albumin preparation as claimed in claim 8, wherein said preparation is in the form of a sterilized aqueous solution.

* * * * *